United States Patent [19]

Kohno

[11] Patent Number: 5,381,225
[45] Date of Patent: Jan. 10, 1995

[54] SURFACE-CONDITION INSPECTION APPARATUS

[75] Inventor: Michio Kohno, Tokyo, Japan

[73] Assignee: Canon Kabushiki Kaisha, Tokyo, Japan

[21] Appl. No.: 199,971

[22] Filed: Feb. 22, 1994

Related U.S. Application Data

[63] Continuation of Ser. No. 84,327, Jun. 30, 1993, abandoned, which is a continuation of Ser. No. 841,845, Feb. 26, 1992, abandoned.

[30] Foreign Application Priority Data

Feb. 28, 1991 [JP] Japan ................. 3-055558

[51] Int. Cl.⁶ .................. G01N 21/88; G01N 21/89
[52] U.S. Cl. .................. 356/237; 356/431; 250/563; 250/572
[58] Field of Search ............ 356/237, 239, 338, 371, 356/445, 446, 429–431, 73; 250/572, 571, 562, 563; 359/619, 202, 203

[56] References Cited

U.S. PATENT DOCUMENTS

| | | | |
|---|---|---|---|
| 3,667,846 | 6/1972 | Nater et al. | 356/376 |
| 4,541,715 | 9/1985 | Akiyama et al. | 356/237 |
| 4,568,835 | 2/1986 | Imamura et al. | 250/572 |
| 4,610,541 | 9/1986 | Tanimoto et al. | 250/563 |
| 4,614,427 | 9/1986 | Koizumi | 356/237 |
| 4,795,911 | 1/1989 | Kohno et al. | 250/572 |
| 4,831,274 | 5/1989 | Kohno et al. | 250/563 |
| 4,871,257 | 10/1989 | Suzuki et al. | 356/237 |
| 4,886,975 | 12/1989 | Murakami et al. | 356/237 |
| 4,999,511 | 3/1991 | Kohno | 356/237 |
| 5,017,798 | 5/1991 | Murakami et al. | 250/572 |
| 5,105,092 | 4/1992 | Natsubori et al. | 250/572 |

FOREIGN PATENT DOCUMENTS 0047641 2/1988 Japan ................. 356/237

Primary Examiner—Richard A. Rosenberger
Assistant Examiner—Hoa Q. Pham
Attorney, Agent, or Firm—Fitzpatrick, Cella, Harper & Scinto

[57] ABSTRACT

An apparatus for inspecting a surface condition of an object having at least a first surface to be inspected and a second surface to be inspected with a higher detection resolution than the first surface includes a holding mechanism, and first and second inspection systems. The holding mechanism holds the object so as to dispose the second surface at a constant position irrespective of the distance between the first and second surfaces. The first and second inspection systems inspect the first and second surfaces of the object, respectively, and each includes an irradiator producing a condensed light beam to illuminate a surface of the object and a receiver for receiving light from a surface of the object. The first and second inspection systems set the angle subtended by the condensed light beam of the first inspection system to be smaller than the angle subtended by the condensed light beam of the second inspection system.

34 Claims, 9 Drawing Sheets

SURFACE-CONDITION INSPECTION APPARATUS

This application is a continuation of application Ser. No. 08/084,327 filed Jun. 30, 1993, now abandoned, which is a continuation of application Ser. No. 07/841,845 filed Feb. 26, 1992, now abandoned.

BACKGROUND OF THE INVENTION

1. Field of the Invention

This invention relates to a surface-condition inspection apparatus, and more particularly, to a surface-condition inspection apparatus which is suitable for detecting a foreign particle, such as dust or the like, adhered to a surface of a photomask or a reticle (hereinafter generically termed a reticle) used in a semiconductor production process by irradiating the surface with a scanning light beam.

2. Description of the Related Art

In the IC (integrated circuit) production process, a pattern for exposure formed on a reticle is in general transferred onto the surface of a semiconductor wafer coated with a resist using a projection optical system or the like of a semiconductor printing apparatus (a stepper or a mask aligner) to produce an IC.

When a pattern is transferred from a reticle onto the surface of a wafer coated with a resist using a semiconductor printing apparatus, if a defect, such as dust or the like, is on the surface of the reticle, the shape of the defect is also printed in addition to the pattern on the reticle, thus causing a decrease in the yield of IC production.

Particularly when a "stepper" is used which prints a desired reticle pattern a plurality of times by a step-and-repeat process, the shape of one particle of dust on the surface of the reticle is printed on the entire surface of the wafer.

Accordingly, it has become important to precisely detect dust on a reticle. Furthermore, it has also become important to provide a shorter inspection time in order to increase the production yield.

FIG. 1 shows a conventional approach for detecting a foreign particle, such as dust or the like, on a reticle. In FIG. 1, a light beam emitted from a laser light source (not shown) is made to be a scanning beam by a rotating element (not shown), such as a polygon mirror or the like, and is condensed onto a reticle 8 via an f-$\theta$ lens 5. In order to shorten inspection time, the beam is divided into upper and lower beams by a half-mirror HM. The two beams are guided and condensed onto the upper surface (a blank surface) "a" and the lower surface (a pattern surface) b of the reticle 8 via reflecting mirrors M1 and M2, respectively. The scanning beams scan the respective surfaces of the reticle 8 in a direction orthogonal to the plane of FIG. 1. The reticle 8 is scanned in the direction $S_1 \rightleftarrows S_2$ in synchronization with the scanning beams, whereby the entire surfaces of the reticle 8 are inspected. If dust is present on a surface of the reticle 8, scattered light of the beam is generated. The scattered light is first imaged onto a field stop 7a or 7b by a condenser lens 6a or 6b (a cylindrical lens having its generatrix in the scanning direction of the beam, a microlens array or the like). The light passing through the aperture of the field stop is guided to a photomultiplier 9a or 9b via optical fibers 8a or 8b. A detection signal from the photomultiplier is guided to a signal processing system (not shown), which processes the signal together with separately-measured scanning position information, whereby the presence and position of dust on each surface are detected.

The influence of dust adhering to the blank surface and the pattern surface of a reticle on a circuit pattern formed on the reticle will now be described. A circuit pattern be transferred to the surface of a wafer is formed on the pattern surface of a reticle in the form of a single-layer chromium film or a double-layer film made of chromium oxide and chromium. The surface of the wafer and the chromium surface are optically conjugate with respect to a printing lens. Hence, the pattern of small dust particles (having the size of 1–2 μm) adhering to the chromium surface is repeatedly transferred onto the surface of the wafer. On the other hand, dust particles having the same size and adhering to the blank surface are defocused and therefore the shape thereof is not transferred thereto. However, dust particles having a large size (at least 5 μm) obturates part of the illuminating light beam (projected from above the reticle) for the portion of the pattern on the chromium surface situated substantially below the dust, thereby causing unevenness in illuminance. As a result, the total integrated amount of illuminating light differs in accordance with the presence/absence of dust for the same exposure time, thereby causing a change in the line width of the circuit pattern.

The minimum resolution required in such an inspection apparatus for detecting dust is 1–2 μm for the pattern surface, and at least 5 μm for the blank surface.

Recently, the size of reticles has increased. While reticles having a size of 5 inches square and 0.09 inch thick have been mainly used for memories having a capacity of equal to or less than 4M (mega) bits, reticles having a size of 6 inches square and 0.25 inch thick are used for 16M-bit memories in accordance with an increase in the size of the printing picture surface. Such a thick reticle may be reused by polishing and removing about 50 μm of the pattern surface for every reuse, If such an operation is repeated 10 times, the thickness of the reticle is reduced by an amount of about 500 μm.

If such reticles having different thicknesses are randomly introduced in an inspection apparatus, the height of the blank surface changes, as shown in FIG. 2 (for example, the upper surface of the reticle 8 changes from a state indicated by solid lines to a state indicated by broken lines), and the diameter of the incident beam on the blank surface of the reticle thereby changes (In this case, the height of the pattern surface does not change even if the thickness of the reticle changes, since the pattern surface (lower surface) contacts a reticle hand 40 when the reticle is supported on the reticle hand). In an inspection apparatus of this kind, since the intensity of light scattered by a particle is inversely proportional to the square of the diameter of the beam, the above-described fact indicates that inspection sensitivity for the blank surface becomes unstable. For example, when a reticle having standard dimensions is inspected, the diameter ($D_0$) of the beam protected on the blank surface of the reticle is assumed to be 30 μm at the cross section of the optical axis, and the incident angle ($\alpha$) of the beam onto the reticle is assumed to be 30°. If a thin reticle having a thickness difference ($\Delta d$) of 500 μm is introduced, the diameter (D') of the beam on the blank surface becomes 40 μm from the following expression (1). Hence, the amount of scattered light is reduced to 56% in the case of a He—Ne laser light source. That is, if dust particles having the minimum size of 5 μm are usually detected with a diameter of the beam of 30 μm, only dust particles having a size of at least 6.7 μm can be detected for a thin reticle.

$$D' = \sqrt{D0^2 + (\Delta d/Fe \sin\alpha)^2}, \text{ where } Fe = \pi D0/4\lambda \quad (1)$$

(λ is the wavelength of the beam).

To sum up, since the shape of dust on the pattern surface is directly transferred, a severe resolution of about 1 μm is required. The resolution is not influenced by the thickness of the reticle. On the other hand, dust on the blank surface functions to produce unevenness in illuminance, and the required resolution may be as large as about 5 μm. However, the resolution is influenced by the thickness of the reticle.

In spite of the above-described difference between the upper and lower surfaces of the reticle, the same light beam is merely divided and guided onto both the pattern surface and the blank surface in the conventional approach shown in FIG. 1. Hence, the conventional approach has the following disadvantage.

That is, since the diameter of the beam is equal on the pattern surface and the blank surface, and since the angle subtended by the beam incident on the upper surface, $2\theta_{BL}$, is equal to the angle subtended by the beam incident on the lower surface, $2\theta_{CR}$, the diameter of the beam on the blank surface is reduced if the diameter ($D_0$) of the beam is reduced in order to increase resolution for a particle on the pattern surface. As a result, the rate of change of the diameter of the beam when a change Δd is produced in the thickness of the reticle also increases from expression (1). This indicates that detection sensitivity changes too much in accordance with a change in the thickness of the reticle.

In order to solve such a problem, a method may be considered wherein the thickness of a reticle is measured in advance, and the focus is readjusted by an amount of a change in the thickness when the blank surface is inspected. This method, however, necessitates a thickness measuring means and a focus adjusting means, thereby causing an increase in the size of the system and in the production cost.

SUMMARY OF THE INVENTION

The present invention has been made in consideration of the disadvantages in the above-described conventional approach.

Accordingly, it is an object of the present invention to overcome the disadvantages of the prior art.

It is another object of the present invention to provide a surface-condition inspection apparatus which can increase its resolution for detecting a foreign particle on surface having a high detection resolution, for example, a pattern surface of a reticle, which can increase the stability of its detection sensitivity for a foreign particle on a surface having a low detection resolution, for example, a blank surface of a reticle, and which can perform detection of foreign particles with high reliability.

According to one aspect, the present invention which achieves these objectives relates to an apparatus for inspecting a surface condition of an object having at least a first surface to be inspected and a second surface to be inspected with a higher detection resolution than the first surface. The apparatus comprises a holding mechanism being configured to hold the object so as to dispose the second surface at a constant position irrespective of the distance between the first surface and the second surface. The apparatus further comprises a first inspection system for inspecting the first surface of the object held by the holding mechanism, comprising an irradiator, producing a first condensed light beam, and a receiver. The first inspection system inspects the first surface by irradiating the first surface with the first condensed light beam from the irradiator and receives light from the first surface irradiated by the first condensed light beam with the receiver. The apparatus further comprises a second inspection system for inspecting the second surface of the object held by the holding mechanism. The second inspection system comprises an irradiator, producing a second condensed light beam, and a receiver. The second inspection system inspects the second surface by irradiating the second surface with the second condensed light beam from the irradiator of the second inspection system and receives light from the second surface irradiated by the second condensed light beam with the receiver of the second inspection system. The first inspection system and the second inspection system set the angle subtended by the first condensed light beam to be smaller than the angle subtended by the second condensed light beam.

The first inspection system includes a first scanning optical system for scanning the first surface with the first condensed light beam and the second inspection system includes a second scanning optical system for scanning the second surface with the second condensed light beam. The first and second scanning optical systems perform beam scanning in substantially parallel directions. The apparatus further comprises a moving mechanism for moving the object in a direction substantially orthogonal to the direction of beam scanning performed by the first and second scanning optical systems.

In one embodiment the object is a reticle and the second surface of the object is a patterned surface of the reticle. In this embodiment the holding mechanism holds the reticle so as to dispose the pattern surface at the constant position.

The first inspection system and the second inspection system can share a common illuminator. In this embodiment the common illuminator comprises a light source, an optical system for condensing light from the light source, and a beam splitter for dividing condensed light from the optical system to form the first condensed light beam and the second condensed light beam. In this embodiment at least one of the first and second inspection systems further includes beam angle conversion means for changing the angle subtended by the beam from the beam splitter.

In another embodiment in which the first inspection system and the second inspection system share a common illuminator, the common illuminator comprises a light source, an optical system for condensing light from the light source, and an optical path switching means for switching the optical path so as to alternately direct condensed light beam from the optical system to the first and second surfaces to be inspected as the first condensed light beams and the second condensed light beam. In this embodiment at least one of the first and second inspection systems includes beam angle conversion means for changing the angle subtended by the beam from the optical path switching means.

In another embodiment in which the first and second optical systems share a common illuminator, the common illuminator comprises a light source and a beam splitter for dividing light from the light source into a first beam and a second beam. In this embodiment the first inspection system includes a first optical system for condensing the first beam to form the first condensed light beam and the second inspection system includes a second optical system for condensing the second beam to form the second condensed light beam. In this embodiment the first optical system is set to produce a beam exiting therefrom which subtends a smaller angle than the beam exiting the second optical system.

In another embodiment the illuminator of the first inspection system includes a first light source and a first optical system for condensing a beam from the first light source. In this embodiment the illuminator of the second inspection means includes a second light source different from the first light source and a second optical system for condensing a beam from the second light source different from the first optical system. In this embodiment the first optional system is set to produce a beam exiting therefrom which subtended a smaller angle than a beam exiting the second optical system.

According to another aspect, the present invention which achieves these objectives relates to an apparatus for inspecting a surface condition of an object having at least a first surface to be inspected and a second surface to be inspected with a higher detection resolution than the first surface. The apparatus comprises a first inspection system for inspecting the first surface of the object, comprising an illuminator producing a first light beam, and a receiver. The first inspection system inspects the first surface by irradiating the first surface with the first light beam from the irradiator of the first inspection system and receives light from the surface irradiated by the first light beam with the receiver of the first inspection system. The apparatus further comprises a second inspection system for inspecting the second surface of the object, comprising an irradiator producing a second beam and a receiver. The second inspection system inspects the second surface by irradiating the second surface with the second light beam from the irradiator of the second inspection system and receives light from the second surface irradiated by the second light beam with the receiver of the second inspection system. The apparatus further comprises a holding mechanism for holding the object. The holding mechanism holds the object so as to dispose the second surface at a constant position with respect to the second inspection system irrespective of the distance between the first surface and the second surface. The first and second inspection systems set the angle subtended by the first light beam to be smaller than the angle subtened by the second light beam.

The first inspection system includes a first scanning optical system for scanning the first surface with the first light beam and the second inspection system includes a second scanning optical system for scanning the second surface with the second light beam. The first and second scanning optical systems perform beam scanning in substantially parallel directions. In this embodiment, the apparatus further comprises a moving mechanism for moving the object in a direction substantially orthogonal to the direction of beam scanning performed by the first and second scanning optical systems.

In one embodiment the object is a reticle and the second surface of the object is a pattern surface of the reticle. In this embodiment the holding mechanism holds the reticle so as to dispose the pattern at the constant position.

The foregoing and other objects and features of the present invention will become more apparent from the following detailed description of the preferred embodiments when taken in connection with the accompanying drawings.

DETAILED DESCRIPTION THE PREFERRED EMBODIMENTS

According to the following preferred embodiments of the present invention, in a surface-condition inspection apparatus for inspecting a surface state of a substrate having a plurality of surfaces to be inspected by condensing and scanning light beams on the substrate and moving the substrate in a direction substantially orthogonal to the scanning direction, the height of a first surface to be inspected, for which high detection resolution is required, is maintained, and the angular aperture of an inspection beam for a second surface to be inspected, for which lower detection resolution is required, is made to be smaller than the angular aperture of a first beam for inspecting the first surface. It is thereby possible to provide stable detection resolution for the second surface even if variations are present in the thickness of the substrate.

Figure 3:
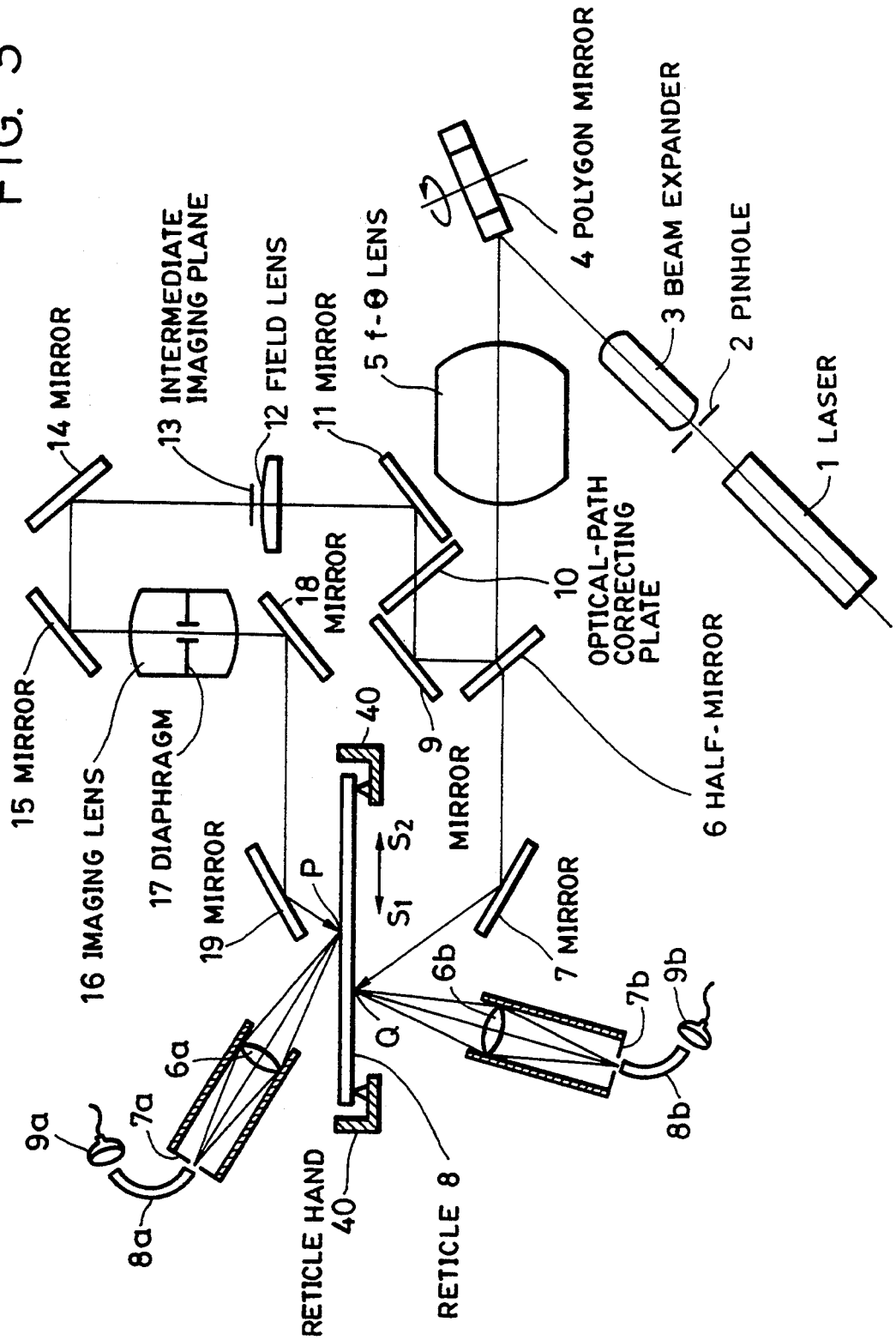
FIG. 3 is a schematic diagram showing the configuration of a first embodiment of the present invention.

FIG. 3 shows the configuration of a first embodiment of the present invention.

Figure 1:
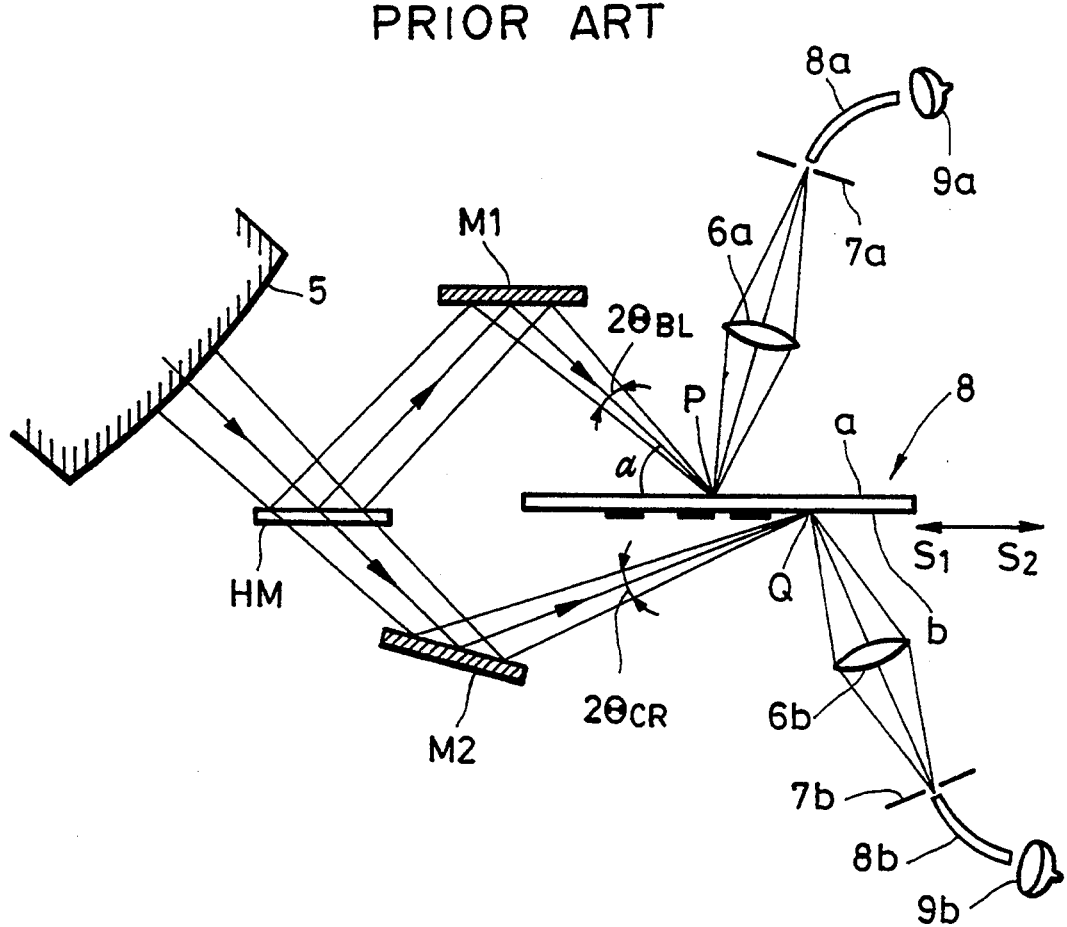
FIG. 1 is a schematic diagram showing the configuration of conventional approach.

The laser beam emitted from a laser light source 1 is shaped into a necessary beam size by a pinhole 2. The shaped beam is then expanded by a beam expander 3, and is incident upon an optical scanner, such as a polygon mirror 4 or the like. The beam reflected by the polygon mirror 4 becomes a converged beam after passing through an f-θ lens 5, and is condensed onto point Q on the lower surface (pattern surface) of a reticle 8 via a half-mirror 6 and a mirror 7. Since the lower surface of the reticle 8 is supported by contacting a reticle hand 40, the height of the reticle 8 is always maintained constant while being moved (That is, the reticle 8 is held at a constant height relative to a detection system at the side of the pattern surface). Part of the converged beam divided by the half-mirror 6 is first intermediately imaged after passing through a mirror 9, an optical-path correcting plate 10, a mirror 11 and a field lens 12. The beam then again becomes divergent, and reaches an imaging lens 16 via mirrors 14 and 15. The imaging lens 16 incorporates an aperture diaphragm 17 for passing part of the beam, and condenses the beam onto point P on the blank surface of the reticle 8 via mirrors 18 and 19. When the polygon mirror 4 rotates via rotating means (not shown), the converged beams scan the upper and lower surfaces of the reticle 8 in a direction orthogonal to the plane of FIG. 3. If the reticle 8 is moved by moving means (not shown) in the direction $S_1 \rightleftarrows S_2$ in synchronization with the beam scanning by synchronization means (not shown), necessary areas to be inspected on the reticle 8 can be inspected. Light-receiving systems may have the same configuration as in the conventional approach (see FIG. 1). However, the light-receiving systems may have any other appropriate configuration.

Figure 4:
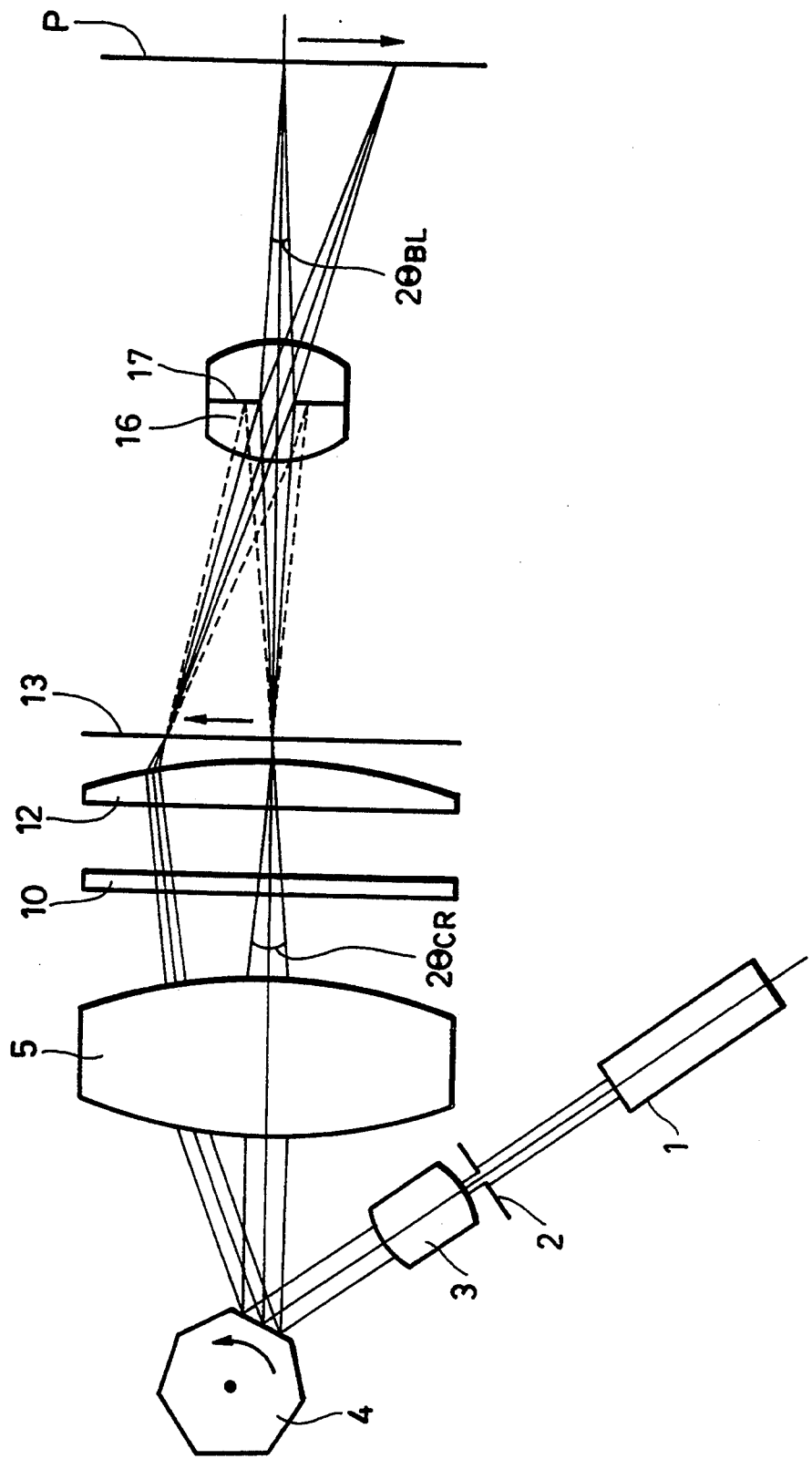
FIG. 4 is a side view of a schematic diagram illustrating the optical relationship of various elements in the first embodiment.

FIG. 4 is a diagram wherein the imaging relationship in the configuration shown in FIG. 3 is optically developed.

The field lens 12 makes the reflection point of the polygon mirror 4 and the center of the diaphragm 17 of the imaging lens 16 to be in a conjugate relationship. According to such an arrangement, a light beam (subtending an angle of $2\theta_{CR}$ as indicated by broken lines) diverging from an arbitrary condensed point of the beam on an intermediate imaging surface 13 is (partially) uniformly obturated by the diaphragm 17 irrespective of the scanning position. As a result, the angle $2\theta_{BL}$ subtended by the beam reimaged onto point P on the blank surface is always smaller than $2\theta_{CR}$ irrespective of the scanning position. The diameter ($D_0$) of a thick beam can be obtained from the following expression (2):

$$D_0 = 4\lambda Fe/\pi = 2\lambda/\pi \sin\theta \qquad (2)$$

It can be understood from the following expression (3) obtained by modifying expression (1) that if the diameter $D_0$ of the beam increases, the rate ($D'/D_0$) of change of the diameter of the beam when the thickness of the reticle changes decreases.

$$D'/D0 = \sqrt{1 + (4\lambda \cdot \Delta d/\pi \sin\alpha)^2 \cdot (1/D0^4)} \qquad (3)$$

Figure 2:
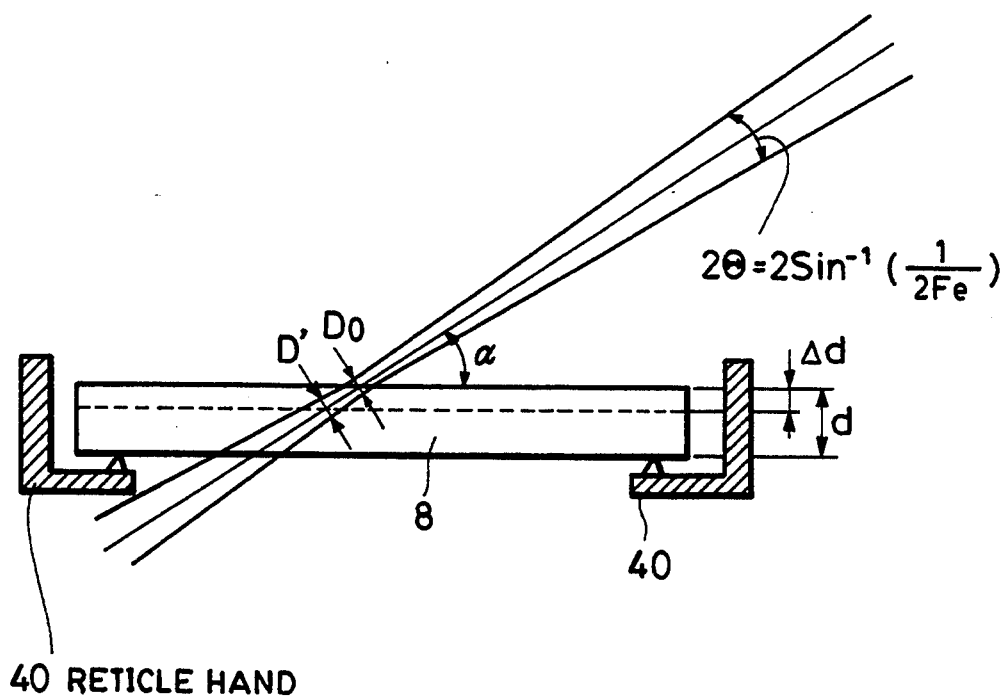
FIG. 2 is a schematic diagram illustrating the relationship between a change in the thickness of a reticle and a change in the diameter of a beam.

Accordingly, the change in detection sensitivity is small even if the position of the blank surface changes as shown in FIG. 2. The beam for the pattern surface is incident upon the the pattern surface without passing through any lens after the half-mirror 6 while maintaining a large angle $\theta$ subtended thereby. Hence, as can be understood from expression (2), the diameter $D_0$ of the beam can be reduced, whereby high resolution can be obtained. As shown in FIG. 4, principal rays (rays in the center of the light beams) incident upon the pattern surface and the blank surface are in general not perpendicular to the scanning line except on the optical axis. In some detection principles, however, it is necesary to make the principal rays perpendicular to the scanning line. This condition is termed a telecentric condition.

In such a case, the principal rays are made to be perpendicular to the scanning line irrespective of the scanning position by adding a field lens near the point Q, seen in FIG. 3, on the pattern surface and adjusting the refractive power of the field lens 12 provided near the intermediate imaging surface 13. A field lens may also be added immediately after the intermediate imaging surface 13. If a similar field lens is added near the point P on the blank surface, it is also possible to make the beam for the blank surface to be telecentric.

In the present embodiment, it is desirable that the imaging magnification from the intermediate imaging surface to the blank surface be unity. This is because an equal beam speed is obtained on both the chromium surface and the blank surface in the case of unit magnification, whereby the same electric circuit may be shared for identifying inspection positions. In the case of a magnification other than unity, different beam speeds may be corrected by separate electric circuits.

In the present embodiment, since inspection beams are simultaneously incident upon the upper and lower surfaces of a reticle, it is possible to simultaneously inspect surface states of both the pattern surface and the blank surface, and therefore to shorten inspection time. Furthermore, since the optical system from the laser to the f-$\theta$ lens can be used as a common optical path for upper and lower beams, it is possible to reduce the size of the entire optical system.

Figure 5:
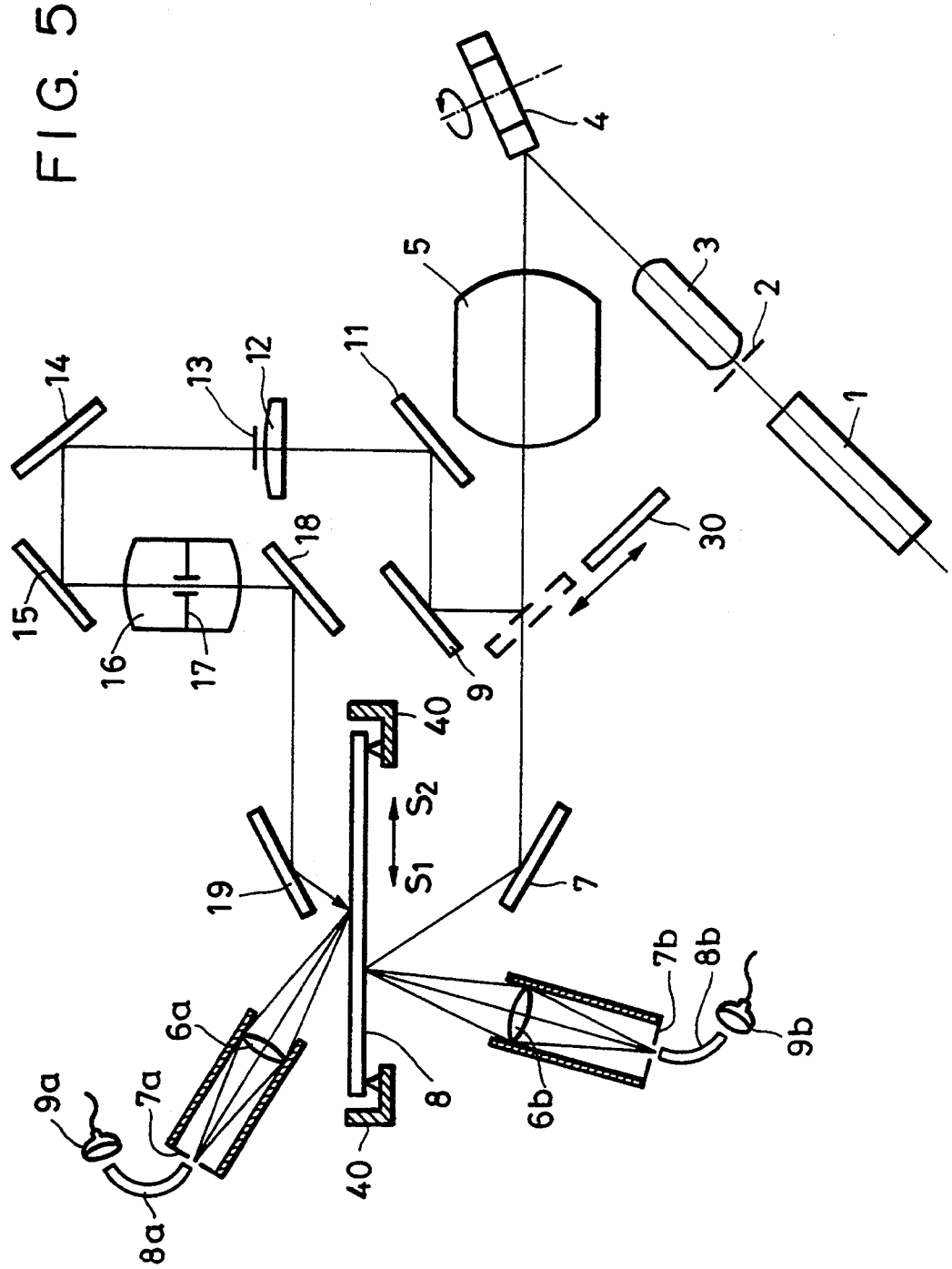
FIG. 5 is a schematic diagram showing the configuration of a second embodiment of the present invention.

FIG. 5 shows the configuration of a second embodiment of the present invention. Similar or identical elements to those shown in FIGS. 3 and 4 are assigned the same reference number. While the present embodiment has the same optical imaging relationship among its elements as the first embodiment, the present embodiment differs from the first embodiment, in that the half-mirror 6 is replaced by a switching mirror 30. While the beams are simultaneously incident upon the upper and lower surface of the reticle in the first embodiment, the upper and lower beams are time serially switched in the present second embodiment. That is, while the reticle is moving in the direction of $S_1 \rightarrow S_2$ during inspection (a foward movement), the switching mirror 30 is retracted from the optical path to condense the beam onto the pattern surface. After the pattern surface has been inspected, the switching mirror 30 is inserted in the optical path to condense the beam onto the blank surface, and the reticle is moved in the direction of $S_2 \rightarrow S_1$ (a backward movement).

According to such an arrangement, it is possible to condense the beam onto the pattern surface or the blank surface without dividing the energy of the beam. Hence, it is possible to increase the amount of light scattered by a foreign particle, and to increase reliability in inspection. Also in the present embodiment, the angle subtended by the beam for the blank surface is made to be smaller than the angle subtended by the beam for the pattern surface by the function of the diaphragm 17, whereby a change in detection sensitivity at the blank surface due to variations in the thickness of the reticle is greatly reduced.

Figure 6:
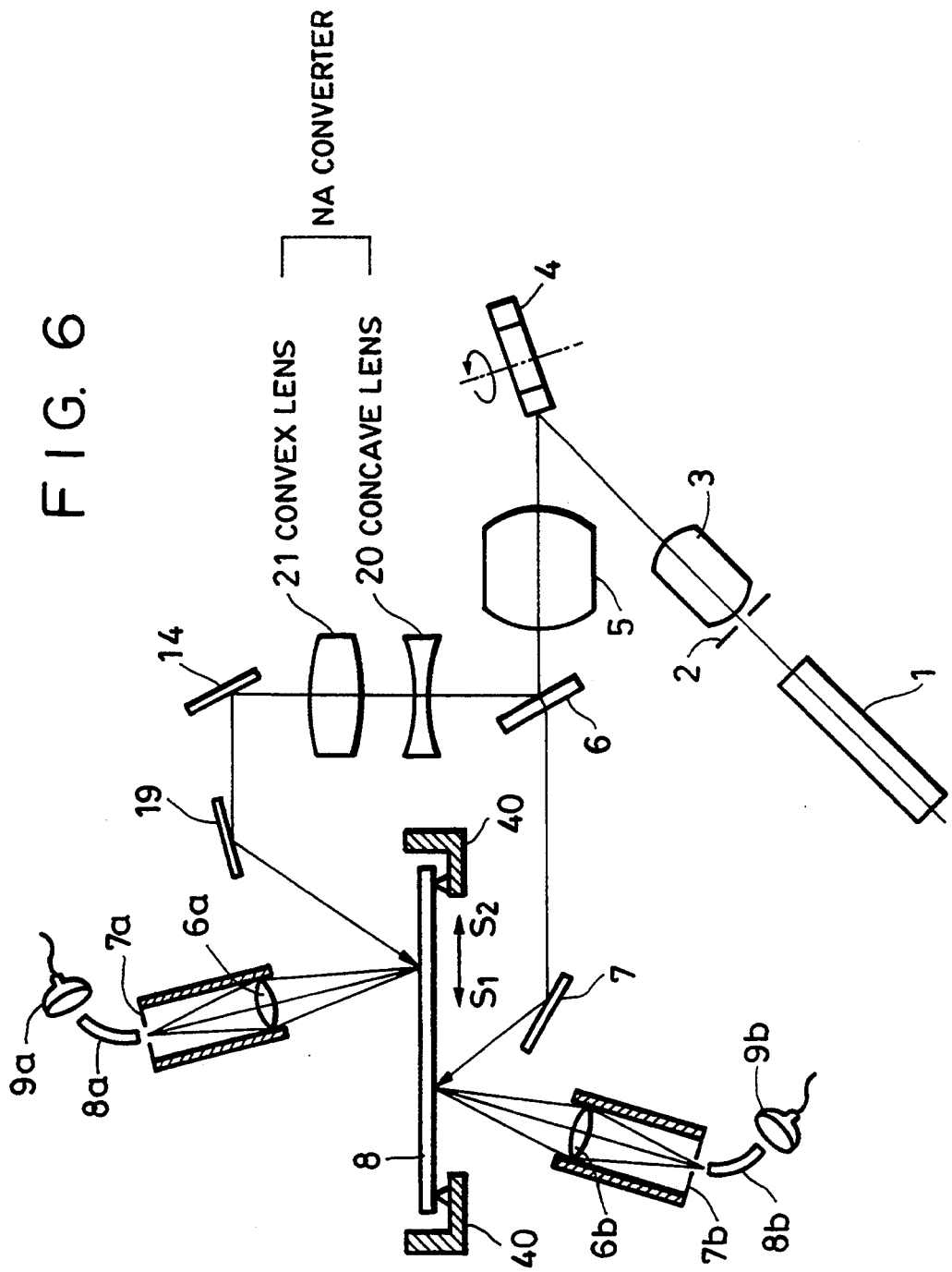
FIG. 6 is a schematic diagram showing the configuration of a third embodiment of the present invention.
Figure 7:
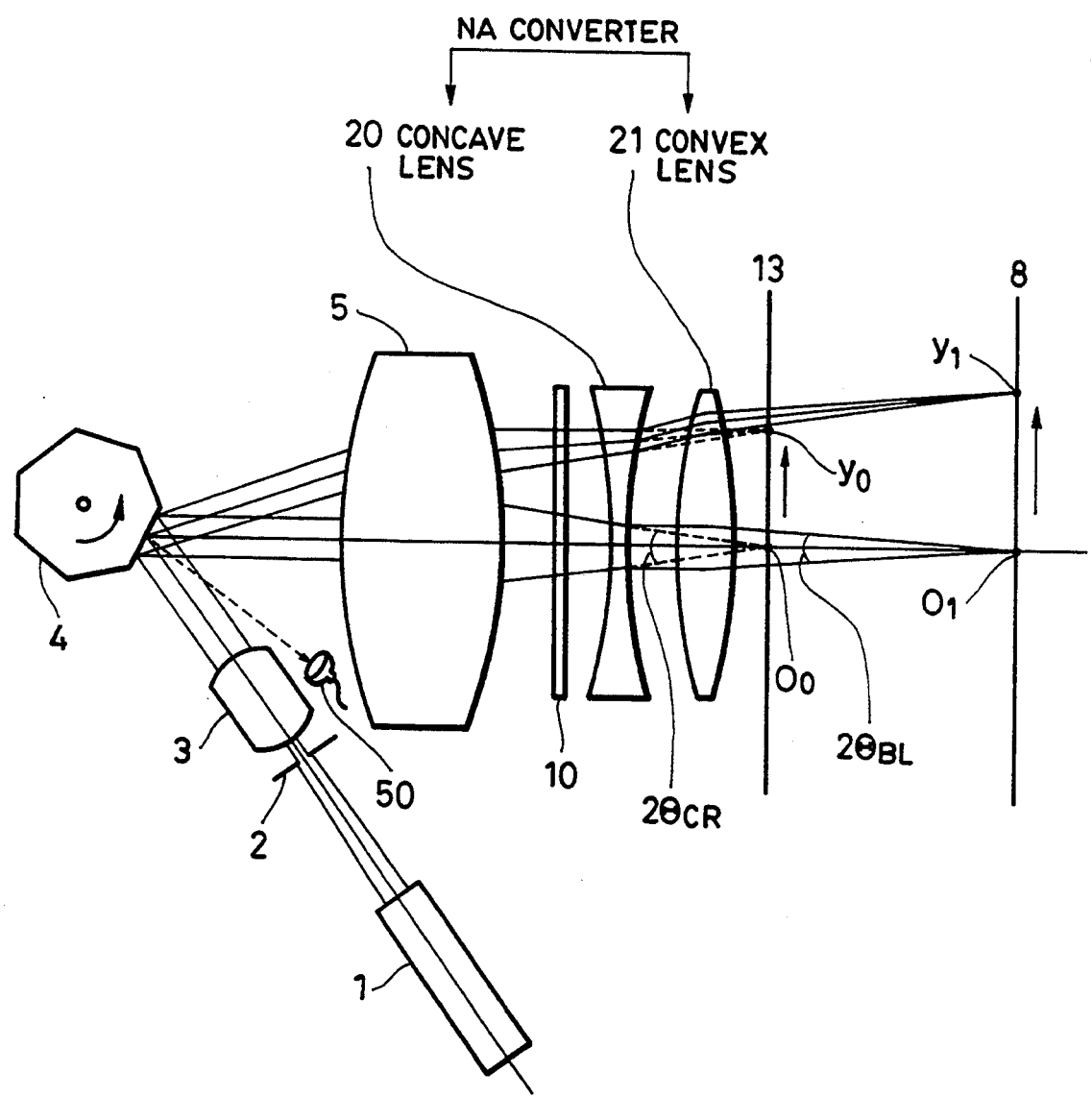
FIG. 7 is a schematic diagram illustrating the optical relationship of various elements in the third embodiment.

FIG. 6 shows the configuration of a third embodiment of the present invention. FIG. 7 shows the optical imaging relationship in the third embodiment. Elements in FIGS. 6 and 7 that are identical or similar to elements in FIGS. 3 and 4 are assigned identical reference numbers.

While the beam for the blank surface is first reimaged and then expanded on the reticle in the first and second embodiments, the present invention has the feature that the beam is expanded without being reimaged. An NA (numerical aperture) converter comprising concave and convex lenses 20 and 21 is provided as a means for enlarging the beam. Other components are the same as those shown in FIG. 3.

The function of the NA converter will be explained with reference to FIG. 7.

The light beam emitted from the laser 1 passes through the f-$\theta$ lens 5, and passes along broken lines and is condensed onto the plane 13 when the concave lens 20 and the convex lens 21 are absent. The light-condensing position of the ray on the optical axis is $O_0$, and the light-condensing position of rays away of the optical axis is $y_0$. The angle subtended by the beam is $2\theta_{CR}$. When the concave lens 20 and the convex lens 21 are present, the beam incident upon the concave lens 20 first becomes a divergent beam, a parallel beam or a weakly-convergent beam by the function of the negative refractive power of the lens, and is incident upon the convex lens 21. The beam again becomes a convergent beam by the function of the convex lens 21 and is condensed onto point $O_1$ on the blank surface of the reticle 8 at the optical axis, and onto point $y_1$ away of the optical axis. The angle $2\theta_{BL}$ subtended by the thus-imaged beam for the blank surface can be made to be smaller than $2\theta_{CR}$ by properly selecting the refractive powers of the lenses 20 and 21 and the interval between the lenses. Hence, a beam for the blank surface having a thick $D_0$ and a small rate of change in detection sensitivity for a change in the thickness of the reticle can be obtained from the above-described expressions (2) and (3).

In the present embodiment, the focal length of the scanning optical system is substantially changed by inserting the NA converter in the optical path. That is, when the NA converter is inserted, the total focal length becomes longer between the polygon mirror 4 and the scanning surface 8 than when only the f-$\theta$ lens 5 is used. As a result, there arises a phenomenon wherein the beam speed differs (as $y_1$ versus $y_0$ in FIG. 7, $y_1$ moves higher than $y_0$) on the pattern surface and the blank surface of the reticle even if the polygon mirror 4 rotates through the same angle. This causes a shift of the inspection position on the blank surface in the scanning direction relative to the inspection position on the chromium surface.

A method of correcting such a shift will now be described. In this method, as shown in FIG. 7, a detector 50 for generating a synchronizing signal is provided as a means for fixing the inspection position (scanning position) on the reticle in order to know the time of rotation of the polygon mirror 4, and a scanning distance on the reticle is measured by a constant delay and a clock pulse counting means. That is, the scanning speed due to the polygon mirror 4 rotating at a constant speed is obtained in advance, and a clock pulse is started by a detection signal of the detector 50. The subsequent scanning position is calculated from the count value (that is, time) of the clock pulses and the scanning speed. In the first and second embodiments, since the upper and lower beams have the same speed, the clock pulses may have the same period in the upper and lower detection systems. In the present embodiment, however, the clock pulses may have different periods in accordance with a difference in the beam speed between the pattern surface and the blank surface. Thus, when a clock pulse at the same count number is generated for each beam, the upper and lower beams irradiate the same position in the scanning direction. Hence, signal processing is simplified.

Figure 8:
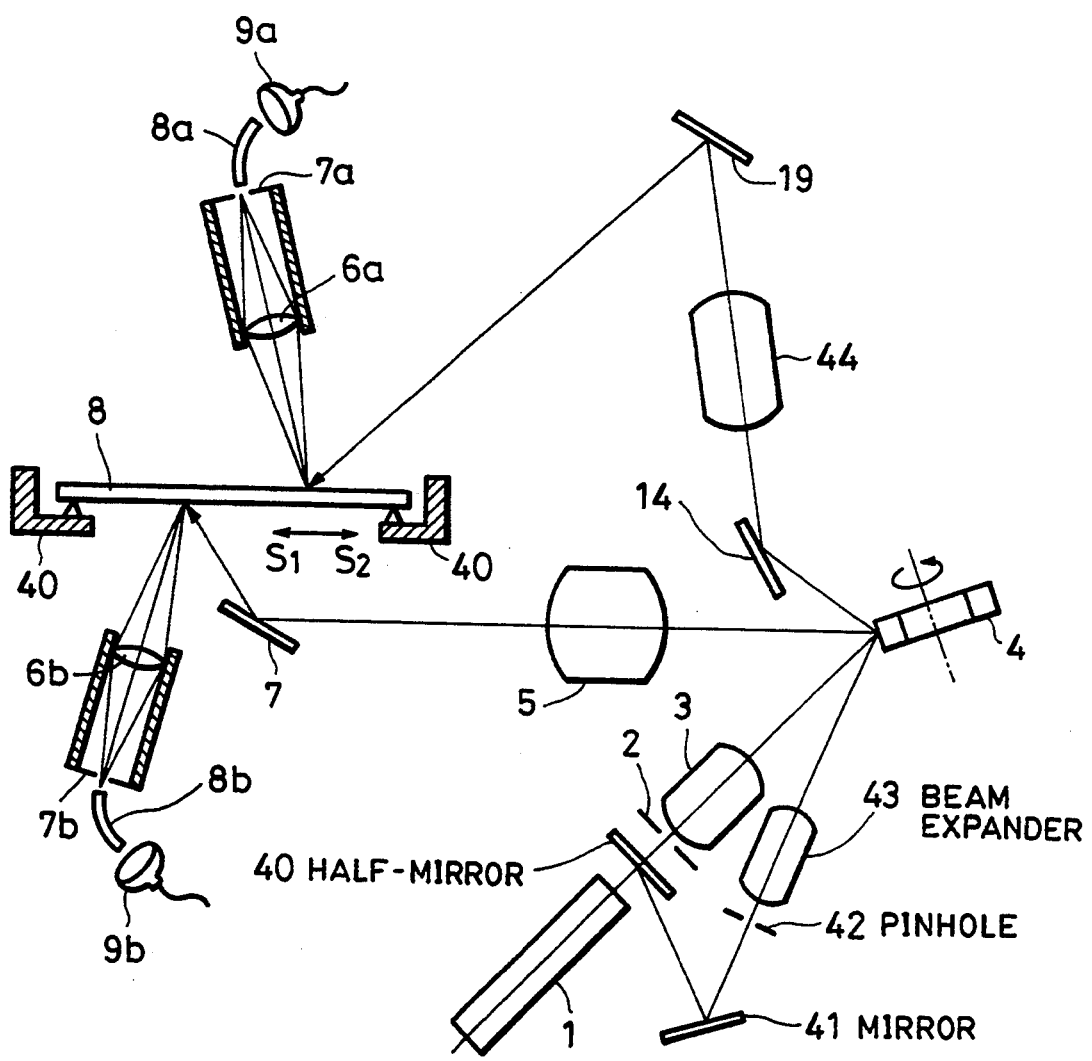
FIG. 8 is a schematic diagram showing the configuration of a fourth embodiment of the present invention.

FIG. 8 shows the configuration of a fourth embodiment of the present invention. Elements in FIG. 8 that are identical or similar to elements in FIGS. 3 and 4 are assigned identical reference numbers.

The present embodiment differs from the first through third embodiments in that the optical paths for the upper and lower beams are separately provided except the polygon mirror 4. That is, as for the beam for the pattern surface, the beam emitted from the laser 1 passes through a half-mirror 40, and is then incident upon the polygon mirror 4 via the pinhole 2 and the beam expander 3. The light reflected by the polygon mirror 4 is guided to the f-$\theta$ lens 5. As for the beam for the blank surface, the beam reflected by the half-mirror 40 is reflected by a mirror 41, and is then made to be a parallel beam thinner than the beam for the pattern surface after passing through a pinhole 42 having a smaller aperture than the pinhole 2, and a beam expander 43 having lower magnification than the beam expander 3. The thin parallel beam is incident upon the polygon mirror 4. The light reflected by the polygon mirror 4 is guided to another f-$\theta$ lens 44, and is finally condensed onto the blank surface as a beam having a thick diameter and subtending a small angle. In this case, it is desirable that the focal length of the f-$\theta$ lens 44 be the same as that of the f-$\theta$ lens 5. If the two focal lengths differ, correction for the scanning speeds may be performed as described in the third embodiment.

Figure 9:
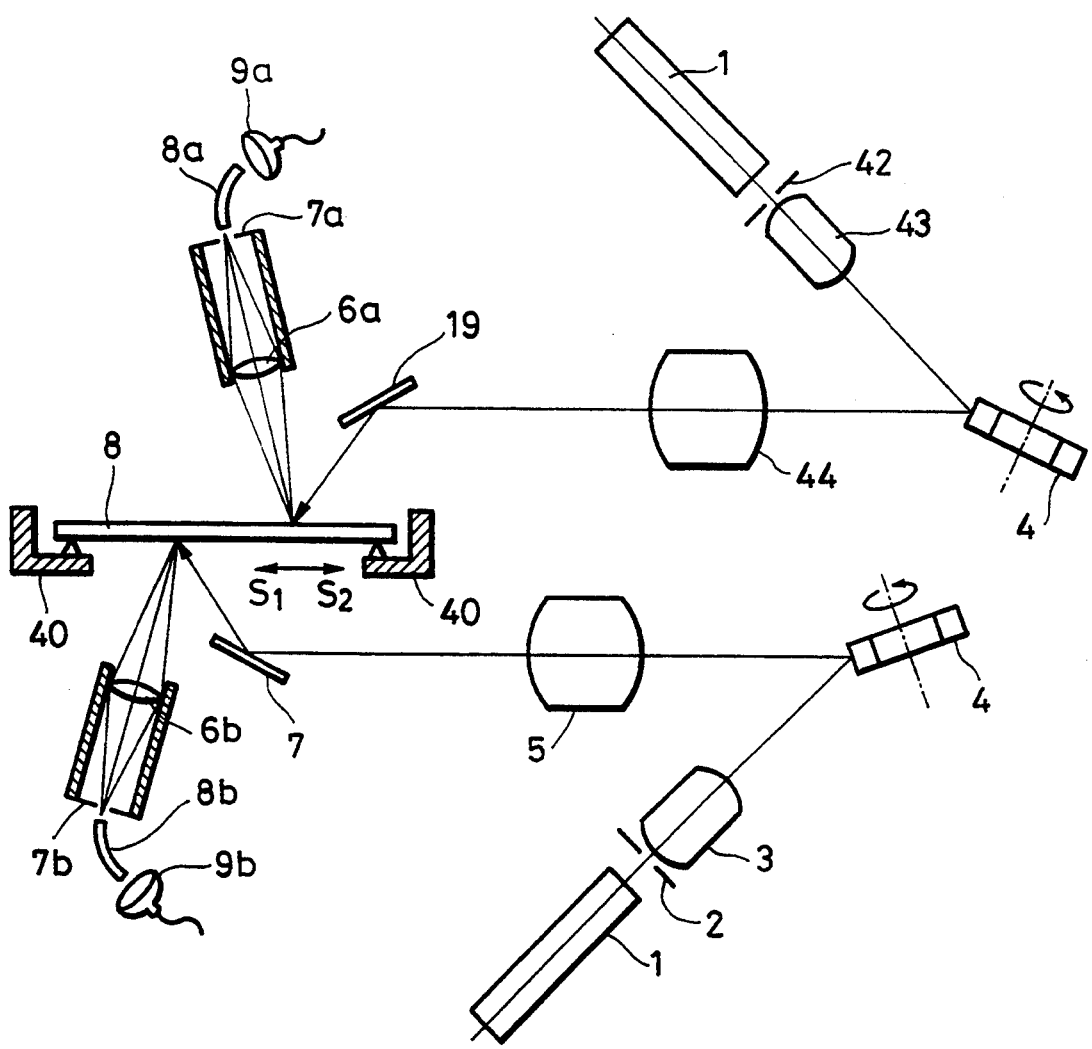
FIG. 9 is a schematic diagram showing the configuration of a fifth embodiment of the present invention.

FIG. 9 shows a fifth embodiment of the present invention. Elements in FIG. 9 that are identical or similar to elements in FIGS. 3 and 4 are assigned identical reference numbers.

The present embodiment has the feature that optical systems for upper and lower beams are completely independently provided. The optical imaging relationship is the same as in the fourth embodiment. The pinhole 42 and the beam expander 43 provided in the optical path for the blank surface have a smaller aperture and smaller magnification than the pinhole 2 and the beam expander 3 for the pattern surface, respectively, as in the fourth embodiment. These components reduce the angle subtended by the beam for the blank surface. By thus individually providing upper and lower optical paths, the number of components increases, but it becomes possible to freely arrange the optical systems.

As explained above, according to the above-described embodiments, it is possible to condense a light beam having a small diameter onto the pattern surface of a reticle, and to condense a light beam subtending a small angle onto the blank surface of the reticle. As a result, it becomes possible to increase the resolution for detecting a foreign particle on the pattern surface, and to stably detect a foreign particle on the blank surface without being influenced by variations in the thickness of the reticle.

Furthermore, since a means for measuring the thickness of a reticle, a means for rearranging the focal length, and the like become unnecessary, it is possible to greatly simplify the system configuration and therefore to reduce the production cost.

Moreover, since a reticle may be reused several times by polishing it, the cost of the entire semiconductor production process can be greatly reduced. The invention also has the ecological effects that resources can be efficiently utilized and the generation of waste can be reduced to a minimum extent.

The optical, mechanical, and electrical elements shown in the drawings are well-known in the optic art and the semiconductor production process art and their specific construction and operation is not critical to the invention or the best mode for carrying out the invention. Therefore, no further description is necessary.

What is claimed is:

1. An apparatus for inspecting a surface condition of an object having at least a first surface to be inspected and a second surface to be inspected with a higher detection resolution than the first surface, said apparatus comprising:

a holding mechanism for holding the object, said holding mechanism being configured to hold the object so as to dispose the second surface at a constant position irrespective of the distance between the first surface and the second surface;

a first inspection system for inspecting the first surface of the object held by said holding mechanism, comprising an irradiator, producing a first condensed light beam of a first diameter, and a receiver, said first inspection system inspecting said first surface by irradiating the first surface with the first condensed light beam from said irradiator and receiving light from the first surface irradiated by the first condensed light beam with said receiver; and a second inspection system for inspecting the second surface of the object held by said holding mechanism, comprising an irradiator, producing a second condensed light beam of a second diameter, greater than the first diameter, and a receiver, said second inspection system inspecting the second surface by irradiating the second surface with the second condensed light beam from said irradiator of said second inspection system and receiving light from the second surface irradiated by the second condensed light beam with said receiver of said second inspection system.

2. An apparatus according to claim 1, wherein said first inspection system includes a first scanning optical system for scanning the first surface with the first condensed light beam, and wherein said second inspection system includes a second scanning optical system for scanning the second surface with the second condensed light beam.

3. An apparatus according to claim 2, wherein said first and second scanning optical systems perform beam scanning in substantially parallel directions, and wherein said apparatus further comprises a moving mechanism for moving the object in a direction substantially orthogonal to the direction of beam scanning direction performed by said first and second scanning optical systems.

4. An apparatus according to claim 1, wherein the object is a reticle, wherein the second surface of the object is a pattern surface of the reticle, and wherein said holding mechanism holds the reticle so as to dispose the pattern surface at the constant position.

5. An apparatus according to claim 1, wherein said first inspection system and said second inspection system comprise a common light source, a common optical system for condensing light from said light source, and a common beam splitter for dividing condensed light from said optical system to form the first condensed light beam and the second condensed light beam, and wherein at least one of said first and second inspection systems further includes beam angle conversion means for changing the angle subtended by the beam from said beam splitter.

6. An apparatus according to claim 1, wherein said first inspection system and said second inspection system comprise a common light source, a common optical system for condensing light from said light source, and a common optical path switching means for switching an optical path so as to alternately direct condensed light from said optical system to the first and second surfaces to be inspected as the first condensed light beam and the second condensed light beam, and wherein at least one of said first and second inspection systems includes beam angle conversion means for changing the angle subtended by the beam from said optical path switching means.

7. An apparatus according to claim 1, wherein said first inspection system and said second inspection system comprise a common light source and beam splitter for dividing light from said light source into a first beam and a second beam, wherein said first inspection system includes a first optical system for condensing the first beam to form the first condensed light beam, wherein said second inspection system includes a second optical system for condensing the second beam to form the second condensed light beam, and wherein said first optical system is set to produce a beam exiting therefrom which subtends a smaller angle than a beam exiting from said second optical system.

8. An apparatus according to claim 1, wherein said irradiator of said first inspection system includes a first light source and a first optical system for condensing a beam from said first light source, wherein said irradiator of said second inspection system includes a second light source different from said first light source, and a second optical system for condensing a beam from said second light source different from said first optical system, and wherein said first optical system is set to produce a beam exiting therefrom which subtends a smaller angle than a beam exiting from said second optical system.

9. An apparatus for inspecting a surface condition of an object having at least a first surface to be inspected and a second surface to be inspected with a higher detection resolution than the first surface, said apparatus comprising:

a first inspection system for inspecting the first surface of the object, comprising an irradiator producing a first light beam of a first diameter, and a receiver, said first inspection system inspecting the first surface by irradiating the first surface with the first light beam from said irradiator of said first inspection system and receiving light from the first surface irradiated by the first light beam with the receiver of said first inspection system;

a second inspection system for inspecting the second surface of the object, comprising an irradiator producing a second beam of a second diameter, larger than the first diameter and a receiver, said second inspection system inspecting the second surface by irradiating the second surface with the second light beam from said irradiator of said second inspection system and receiving light from the second surface irradiated by the second light beam with the receiver of said second inspection system; and a holding mechanism for holding the object, said holding mechanism holding the object so as to dispose the second surface at a constant position with respect to said second inspection system irrespective of the distance between the first surface and the second surface.

10. An apparatus according to claim 9, wherein said first inspection system includes a first scanning optical system for scanning the first surface with the first light beam, and wherein said second inspection system includes a second scanning optical system for scanning the second surface with the second light beam.

11. An apparatus according to claim 10, wherein said first and second scanning optical systems perform beam scanning in substantially parallel directions, and wherein said apparatus further comprises a moving mechanism for moving the object in a direction substantially orthogonal to the direction of beam scanning performed by said first and second scanning optical systems.

12. An apparatus according to claim 9, wherein the object is a reticle, wherein the second surface of the object is a pattern surface of the reticle, and wherein said holding mechanism holds the reticle so as to dispose the pattern surface at the constant position.

13. An apparatus for inspecting a surface condition of an object having at least a first surface to be inspected and a second surface to be inspected with a higher detection resolution than the first surface, said apparatus comprising:

a first inspection system for inspecting the first surface of the object, comprising an irradiator, producing a first condensed light beam of a first diameter, and a receiver, said first inspection system inspecting said first surface by irradiating the first surface with the first condensed light beam from said irradiator and receiving light from the first surface irradiated by the first condensed light beam with said receiver; and a second inspection system for inspecting the second surface of the object, comprising an irradiator, producing a second condensed light beam of a second diameter, greater than the first diameter, and a receiver, said second inspection system inspecting the second surface by irradiating the second surface with the second condensed light beam from said irradiator of said second inspection system and receiving light from the second surface irradiated by the second condensed light beam with said receiver of said second inspection system.

14. An apparatus according to claim 13, wherein said first inspection system includes a first scanning optical system for scanning the first surface with the first condensed light beam, and wherein said second inspection system includes a second scanning optical system for scanning the second surface with the second condensed light beam.

15. An apparatus according to claim 14, wherein said first and second scanning optical systems perform beam scanning in substantially parallel directions, and wherein said apparatus further comprises a moving mechanism for moving the object in a direction substantially orthogonal to the direction of beam scanning direction performed by said first and second scanning optical systems.

16. An apparatus according to claim 13, wherein the object is a reticle, wherein the second surface of the object is a pattern surface of the reticle, and wherein said apparatus further comprises a holding mechanism holding the reticle so as to dispose the pattern surface at the constant position.

17. An apparatus according to claim 13, wherein said first inspection system and said second inspection system comprise a common light source, a common optical system for condensing light from said light source, and a common beam splitter for dividing condensed light from said optical system to form the first condensed light beam and the second condensed light beam, and wherein at least one of said first and second inspection systems further includes beam angle conversion means for changing the angle subtended by the beam from said beam splitter.

18. An apparatus according to claim 13, wherein said first inspection system and said second inspection system comprise a common light source, a common optical system for condensing light from said light source, and a common optical path switching means for switching an optical path so as to alternately direct condensed light from said optical system to the first and second surfaces to be inspected as the first condensed light beam and the second condensed light beam, and wherein at least one of said first and second inspection systems includes beam angle conversion means for changing the angle subtended by the beam from said optical path switching means.

19. An apparatus according to claim 13, wherein said first inspection system and said second inspection system comprise a common light source and beam splitter for dividing light from said light source into a first beam and a second beam, wherein said first inspection system includes a first optical system for condensing the first beam to form the first condensed light beam, wherein said second inspection system includes a second optical system for condensing the second beam to form the second condensed light beam, and wherein said first optical system is set to produce a beam exiting therefrom which subtends a smaller angle than a beam exiting from said second optical system.

20. An apparatus according to claim 13, wherein said irradiator of said first inspection system includes a first light source and a first optical system for condensing a beam from said first light source, wherein said irradiator of said second inspection system includes a second light source different from said first light source, and a second optical system for condensing a beam from said second light source different from said first optical system, and wherein said first optical system is set to produce a beam exiting therefrom which subtends a smaller angle than a beam exiting from said second optical system.

21. An apparatus for optically inspecting a surface condition of a first surface and for optically inspecting a surface condition of a second surface with a lower detection resolution than the first surface, said apparatus comprising:

a first irradiating optical system for irradiating the first surface with a first light beam in order to inspect the first surface; and a second irradiating optical system for irradiating the second surface with a second light beam having an opening angle smaller than that of the first light beam, in order to inspect the second surface.

22. An apparatus according to claim 21, wherein said first and second irradiating optical systems scan the first surface with the first light beam and the second surface with the second light beam, respectively.

23. An apparatus according to claim 22, wherein said first and second irradiating optical systems share a common optical system for the scanning operation.

24. An apparatus according to claim 21, further comprising a first photodetector for detecting scattered light generated by irradiation of the first light beam on the first surface, and a second photodetector for detecting scattered light generated by irradiation of the second light beam on the second surface.

25. An apparatus according to claim 24, wherein said first and second irradiating optical systems scan the first surface with the first light beam and the second surface with the second light beam, respectively.

26. An apparatus according to claim 25, wherein said first and second irradiating optical systems share a common optical system for the scanning operation.

27. An apparatus for optically inspecting a surface condition of each of the both sides of an original, wherein a pattern to be projected from the original is formed on a surface of one side of the original, said apparatus comprising:
- a first irradiating optical system for irradiating a surface of the one side of the original with a first light beam in order to inspect the surface of the one side of the original; and
- a second irradiating optical system for irradiating a surface of the other side of the original, with a second light beam having an opening angle smaller than that of the first light beam, in order to inspect the surface of the other side of the original.

28. An apparatus according to claim 27, said first and second irradiating optical systems scan the surface of the one side of the original with the first light beam and the surface of the other side of the original with the second light beam, respectively.

29. An apparatus according to claim 28, wherein said first and second irradiating optical systems share a common optical system for the scanning operation.

30. An apparatus according to claim 29, further comprising a laser for supplying the first and second light beams.

31. An apparatus according to claim 27, further comprising a first photodetector for detecting scattered light generated by irradiation of the first light beam on the surface of the one side of the original and a second photodetector for detecting scattered light generated by irradiation of the second light beam on the surface of the other side of the original.

32. An apparatus according to claim 31, wherein said first and second irradiating optical systems scan the surface of the one side of the original with the first light beam and the surface of the other side of the original with the second light beam, respectively.

33. An apparatus according to claim 32, wherein said first and second irradiating optical systems share a common optical system for the scanning operation.

34. An apparatus according to claim 31, further comprising a laser for supplying the first light beam and the second light beam.

* * * * *

UNITED STATES PATENT AND TRADEMARK OFFICE
CERTIFICATE OF CORRECTION

PATENT NO. : 5,381,225            Page 1 of 2
DATED : January 10, 1995
INVENTOR(S) : MICHIO KOHNO It is certified that error appears in the above-indentified patent and that said Letters Patent is hereby corrected as shown below:

COLUMN 2

Line 19, "obturates" should read --obturate--.
Line 59, "protected" should read --projected--.

COLUMN 3

Line 6, "DO$^2$" should read --Do$^2$--; and "$\pi DO/4\lambda$" should read --$\pi Do/4\lambda$--.

COLUMN 5

Line 51, "subtened" should read --subtended--.

COLUMN 7

Line 45, "D'/DO" should read --D'/Do--; and "(1/DO$^4$)" should read --(1/Do$^4$)--.

COLUMN 11

Line 49, "direction" should be deleted.

COLUMN 13

Line 56, "direction" should be deleted.

COLUMN 14

Line 48, "than" should read --than for--.

UNITED STATES PATENT AND TRADEMARK OFFICE
CERTIFICATE OF CORRECTION

PATENT NO. : 5,381,225     Page 2 of 2

DATED : January 10, 1995

INVENTOR(S) : MICHIO KOHNO

It is certified that error appears in the above-indentified patent and that said Letters Patent is hereby corrected as shown below:

<u>COLUMN 15</u>

Line 11, "the both" should read --both--.
    Line 25, "said" should read --wherein said--.

Signed and Sealed this

Sixteenth Day of May, 1995

Attest:

BRUCE LEHMAN

*Attesting Officer*      *Commissioner of Patents and Trademarks*